United States Patent
Huluka

(10) Patent No.: US 10,234,440 B2
(45) Date of Patent: Mar. 19, 2019

(54) METHODS FOR PREPARING BUFFER SOLUTIONS AND PREDICTING ACIDIC AMENDMENT REQUIREMENTS IN SOILS

(71) Applicant: Gobena Huluka, Auburn, AL (US)

(72) Inventor: Gobena Huluka, Auburn, AL (US)

( * ) Notice: Subject to any disclaimer, the term of this patent is extended or adjusted under 35 U.S.C. 154(b) by 457 days.

(21) Appl. No.: 14/928,065

(22) Filed: Oct. 30, 2015

(65) Prior Publication Data

US 2016/0123952 A1    May 5, 2016

Related U.S. Application Data

(60) Provisional application No. 62/074,371, filed on Nov. 3, 2014.

(51) Int. Cl.
*G01N 33/24* (2006.01)

(52) U.S. Cl.
CPC ....... *G01N 33/24* (2013.01); *G01N 2033/245* (2013.01)

(58) Field of Classification Search
None
See application file for complete search history.

(56) References Cited

U.S. PATENT DOCUMENTS

| | | | | |
|---|---|---|---|---|
| 1,520,891 | A | * | 12/1924 | Spurway ............... 436/163 |
| 2,604,382 | A | * | 7/1952 | Woodruff ............... G01N 33/24 324/101 |
| 5,514,639 | A | | 5/1996 | Fisher et al. |
| 6,287,357 | B1 | | 9/2001 | Lynch et al. |
| 6,541,421 | B1 | | 4/2003 | Forsyth et al. |
| 7,679,058 | B2 | | 3/2010 | Kissel et al. |
| 8,133,294 | B2 | | 3/2012 | Whitehurst et al. |
| 2010/0129474 | A1 | | 5/2010 | Benjamin et al. |

OTHER PUBLICATIONS

Mickelbart, M.V. et al. Purdue Extension publication HO-241-W "Commercial Greenhouse and Nursery Production: Lowering Soil pH for Horticulture Crops," Apr. 4, 2012. (Year: 2012).*

Mickelbart, M.V. et al. Purdue Extension publication HO-240-W "Commercial Greenhouse and Nursery Production: Soil pH," Apr. 4, 2012. (Year: 2012).*

Huluka, G. "A Modification to the Adams-Evans Soil Buffer Determination Solution," Communications in Soil Science and Plant Analysis, 36: 2005-2014, 2005. (Year: 2005).*

(Continued)

*Primary Examiner* — Lyle Alexander
*Assistant Examiner* — Michelle Adams
(74) *Attorney, Agent, or Firm* — Philip H. Burrus, IV

(57) ABSTRACT

A method and system for testing soil includes wetting a selected soil sample to obtain a soil solution and measuring an initial pH of the soil solution. A buffer solution is then applied to the soil solution to displace alkaline anions from soil colloids of the soil solution with a displacement agent and to neutralize the alkaline anions with a neutralization agent in a buffer having a buffer pH of between 4.38 and 4.42. A resultant pH of the soil solution is then measured. A target pH for the soil sample is selected, and using mathematical relationships of the disclosure, an acidic amendment recommendation is obtained as a function of the initial pH, the resultant pH, and the target pH.

15 Claims, 6 Drawing Sheets

(56) References Cited

OTHER PUBLICATIONS

"SAS/STAT User's Guide", vol. 1, ANOVA-FREQ; Version 6 Fourth Addition; 1990, first page of Chapter 1: Introduction to Regression Procedures.

Adams, Fred et al., "A Rapid Method for Measuring Lime Requirement of Red-Yellow Podzolic Soilds", Published in 1962; Soil Science Society Proceedings.

Huluka, Gobena, "A Modification to the Adams-Evans Soil Buffer Determination Solution", Communications in Soil Science and Plant Analysis, 36; 2005-2014; Published 2005.

Liu, Min et al., "Soil Lime Requirement by Direct Titration with Calcium Hydroxide", Published by Soil Science Society of America Journal; Jul. 2004.

Mehlich, A, "New buffer pH method for rapid estimation of exchangeable acidity and lime requirement of soils", Communications in Soil Science and Plant Analysis; https://doi.org/10.1080/00103627609366673; Nov. 11, 2008.

Mitchel, Charles et al., "Lowering Soil pH", Alabama Cooperative Extension; Agronomy and Soils Series; Apr. 2008.

Shoemaker, H. E. et al., "Buffer Methods for Determining Lime Requirement of Soils with Appreciable Amounts of Extractable Aluminum", Division II—Soil Chemistry; Published Jul. 1961.

Teem, David, "Procedures used for soil and plant analysis by the Auburn University Soil Testing Laboratory", Published in Jan. 1986; Auburn University Department of Agronomy and Soils Departmental Series No. 106.

\* cited by examiner

METHODS FOR PREPARING BUFFER SOLUTIONS AND PREDICTING ACIDIC AMENDMENT REQUIREMENTS IN SOILS

CROSS REFERENCE TO PRIOR APPLICATIONS

This application claims priority and benefit under 35 U.S.C. § 119(e) from U.S. Provisional Application No. 62/074,371, filed Nov. 3, 2014, which is incorporated by reference for all purposes.

BACKGROUND

Technical Field

This disclosure relates generally to systems and methods for testing soil, and more particularly to systems and methods for predicting an amount of acid to add to a given soil to reduce the soil pH to a target level.

Background Art

Some soils have a soil pH that is higher than desired for a given crop to grow optimally. Blueberries, azaleas, and other crops perform better and produce greater yields in soils having lower soil pH levels. Blueberries, for instance, generally perform better when grown in soils having a soil pH of between 5.0 and 5.5. However, most agricultural soils in the southeastern United States have a soil pH in the range of 5.0 to 7.0 due to the abundant precipitation that occurs in the region annually. Thus, it would not be uncommon to encounter a soil in the southeastern United States with a soil pH between, for example, 6.0 and 7.0.

Moreover, even if the soil pH may naturally tend to be within a range desirable for growing a lower soil pH crop, over liming and other factors such as high concentrations of hydroxide ions, or carbonate ions, or bicarbonate ions can artificially increase the pH of a particular soil. Illustrating bye example, in the southeastern United States where the soils are poorly buffered and do not have a lot of cations, small applications of lime can cause radical changes in soil pH. The pH of less buffered soils can change from 4 to 8 simply by applying a small amount of lime.

Where the soil pH is above the desired range, yields of blueberries and other crops can be reduced. It would therefore be desirable to have systems, buffer solutions, and methods to accurately assess necessary acidic amendment requirements to reduce the pH of a soil to a target level.

Figure 1:
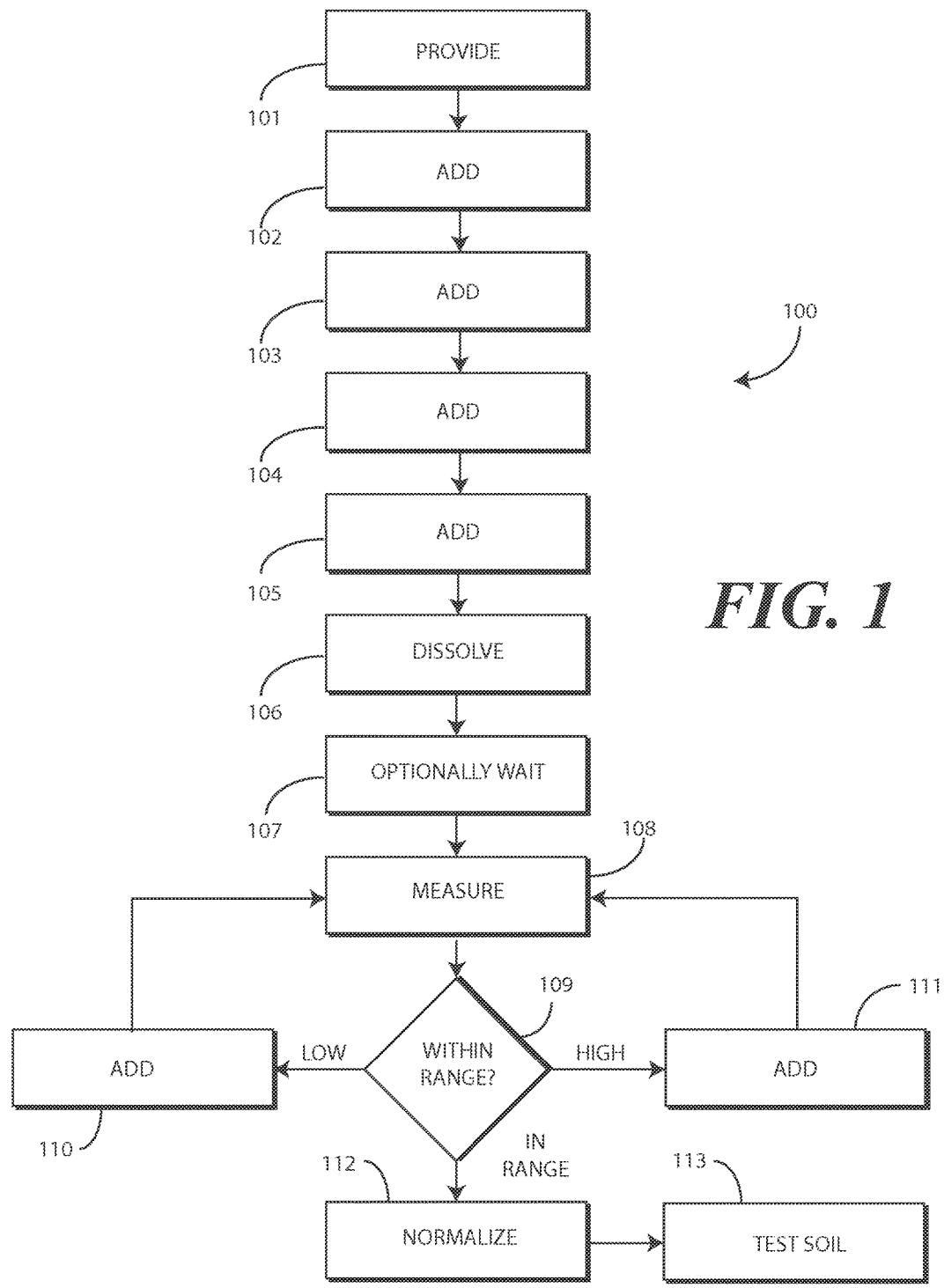
FIG. 1 illustrates one explanatory method in accordance with one or more embodiments of the disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

Before describing in detail embodiments that are in accordance with the present disclosure, it should be observed that the embodiments reside primarily in combinations of method steps and system components related to accurately assessing necessary acidic amendment requirements to reduce the pH of a soil to a target level. Alternate implementations are included, and it will be clear that steps may be executed out of order from that shown or discussed, including substantially concurrently or in reverse order, depending on the functionality involved. Accordingly, the system components and method steps have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, it is expected that one of ordinary skill, notwithstanding possibly significant effort and many design choices motivated by, for example, available time, current technology, and economic considerations, when guided by the concepts and principles disclosed herein will be readily capable of generating such system components and buffer solutions, as well as executing such methods described below, with minimal experimentation.

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the present disclosure provide systems and methods for predicting an acidic amendment requirement, such as elemental sulfur, alum, or iron sulfate, in soil to achieve a target pH. The ability to accurately predict the acidic amendment requirement is important for decreasing the pH of soils in which crops such as blueberries or azaleas are grown. Basic or neutral soils affect root growth and, ultimately, crop yield for crops that prefer lower pH soils.

Embodiments of the disclosure provide methods and buffer solutions for scientifically determining acidifying amendment material recommendations for lowering the pH of a selected soil. In one embodiment, a buffer solution for testing soil includes a soil colloid alkaline anion displacement agent. The soil colloid alkaline anion displacement agent can be ammonium fluoride in one embodiment. In alternate embodiments, the soil colloid alkaline anion displacement agent can comprise monopotassium phosphate.

In one embodiment, the buffer solution also includes a buffer comprising a combination of monobasic potassium phosphate and ammonium acetate. A soil colloid alkaline anion neutralization agent is also included. In one embodiment, the soil colloid alkaline anion neutralization agent comprises acetic acid. These components are mixed into a solution along with one or more of deionized water or distilled water to create a buffer solution where the buffer buffers the solution at a pH between 4.0 and 5.0, and preferably between 4.38 and 4.44.

The buffer solution can then be used in a method to obtain an acidic amendment recommendation expressed in weight of the amendment per area of soil. In one embodiment, a method of testing a selected soil includes wetting the selected soil sample with one of deionized water or distilled water to obtain a soil solution. For example, in one embodiment a ten-gram sample of dry soil can be mixed with ten milliliters of deionized water to obtain a soil solution. After optionally waiting for a predetermined time, such as ten minutes, the method includes measuring an initial pH of the soil solution.

After measuring the initial pH, in one embodiment the method includes applying a buffer solution to the soil solution. The buffer solution then works to displace alkaline anions from soil colloids of the soil solution with a displacement agent. Those displaced alkaline ions are then neutralized by a neutralization agent in a buffer having a buffer pH of between 4.0 and 5.0, and preferably between 4.38 and 4.42. After the buffer solution is applied, the method measures a resultant pH of the soil solution.

Using a selected target pH for the selected soil sample, tables or mathematical equations then allow an acidic amendment requirement to be obtained. In one or more embodiments, this acidic amendment requirement is a function of the initial pH, the resultant pH, and the target pH. The acidic amendment requirement can also be a function of the exchangeable basicity of the selected soil sample. The exchangeable basicity can be either calculated or estimated.

Soils have different pH values due to soil forming processes and/or anthropogenic activities. The dominant soils in southeastern United States, for example, can be naturally acidic and unbuffered. Parent materials of the soils and climatic conditions that prevail in the regions have played significant roles in reaching this condition. Most agricultural soils in southeastern United States receive abundant precipitation, resulting in the soils having a typical pH of between 5.0 and 7.0. Abundant rain washes basic cations such as calcium ($Ca^{2+}$), magnesium ($Mg^{2+}$), potassium ($K^+$), and others down the soil profile. This leaves acidic cations such as hydrogen ($H^+$), aluminum ($Al^{+3}$), and iron ($Fe^{3+}$) adsorbed on topsoil soil colloids. The region is also dominated with ultisols that have low activity clay and in general poorly buffered. Consequently, base cations of the soil colloids are easily displaced by acidic cations such as hydrogen ions and aluminum ions.

This displacement by acidic cations can require the application of lime to increase soil pH, as doing so is agronomically desirable in some instances. To be sure, the application of lime is a common agricultural practice in the southeastern United States Over application of lime, however, or the application of lime to high pH soils can be detrimental.

The need to accurately predict liming requirements, as well as the natural state of soils in the region, has led to the development of acid buffer solutions, such as those developed by Adams and Evans in 1962, by Mehlich in 1967, and by Shoemaker et al. in 1961. The Adams and Evans buffer and the Mehlich buffer are both widely used in the southeastern United States due to the fact that yield in crops such as corn, cotton, peanut, and others can be significantly reduced when those crops are grown in low pH soils. The pH can be lower than desirable due to the leaching of basic cations such as calcium, potassium, and magnesium with accompanying anions such as nitrate ($NO_3^-$), sulfate ($SO_4^{2-}$), and carbonate ($CO_3^{2-}$). It should be noted that one criticism of acid buffer solutions such as the Adams Evans and Shoemaker buffers is the potential toxicity associated with each, as both solutions contain p-nitrophenol.

While predicting the proper liming requirement has been well studied, embodiments of the present disclosure understand that the ability to predict the proper acidic amendment requirement has not. Although liming determination and buffers are well developed, there is a lack of a rapid method to determine the amount of acidifying materials that can be applied to soil to reach a target pH.

Embodiments of the disclosure contemplate that even though the need for acidifying soils is not as common as the need for liming, it is also advantageous to be able to determine what amounts of amendments should be added to the soil to lower the soil pH to a target level to fit the need of acid loving plants such as blueberries, azaleas and others. Embodiments of the disclosure understand that 3 here are conditions when it becomes necessary to decrease soil pH to specific values for agronomic purposes. Embodiments of the disclosure contemplate that little to no research has been conducted to develop an acceptable method that can be used to determine the amount of an acidifying substance to apply to the soil for a target pH value. It is known that the application of acidifying amendments such as elemental sulfur, dilute sulfuric acid, aluminum sulfate ("alum"), ferrous sulfate, reduced nitrogen and sulfur containing fertilizers, and organic materials can lower soil pH. However, to date accurately predicting how much of these materials should be added to achieve a target pH is not well understood. Embodiments of the disclosure advantageously offer a rapid, inexpensive, and accurate method and system, suitable for wide scale laboratory use, which determines a recommendation amount of acidifying materials needed to lower a soil pH.

Prior art techniques attempting to determine a recommendation amount of sulfur or other similarly functioning materials to be applied to a given soil to reduce its pH have been as a function of soil textural class. The assumption underlying this process is that clay soils have more surface area and more buffer sites on the colloids than, for example, do sand soils. This means that clay soil colloids can potentially bind to larger numbers of hydroxide ions, or carbonate ions, or bicarbonate ions than will sand. Accordingly, a soil having more clay will likely require more acidic amendments to reduce a soil pH than will a soil having more silt or sand. In effect, prior art methods assume clayey soils always have more concentration of high pH causing anions regardless of their type, parent materials, and/or corresponding percentages of sand and silt Using soil texture, prior art methods simply empirically estimate the amount of acidifying materials needed to reduce soil pH to a target value. Even though soil textural classification is an important soil physical property, there is little scientific basis to relate texture to the buffering capacity of a soil. While it is true that clayey soils are more buffered compared to sandy soils, it is not necessarily correct to assume that all cations on soil colloids are basic cations.

Also, the broad classification of clayey, loam and sand does not quantify the contribution of each of the textural components. A Soil that contains more than sixty percent clay is classified as a clay soil based on United States Department of Agriculture. Using prior art methods, a soil that has seventy-five percent clay will be treated exactly the same as another soil that has only sixty-percent clay, and will receive the same recommendation of acidifying material despite the fact that they have very different clay content amounts. The same is true loamy and sandy soils. The prior art methods therefore fail to address the need for accurate amount of acidifying materials for all soil textural classes.

The soil texture based acid recommendation method therefore has many inadequacies. To begin, it is an empirical method that fails to quantify the buffering capacity, i.e., the amount of basicity present in the soil. Hydroxyl ions ($OH^-$), bicarbonate ($HCO_3^-$) and carbonate ($CO_3^{2-}$) are the anions that cause an elevated soil pH. The prior art method fails to estimate the amount of these anions in the soil. The prior art method is anecdotal at best, and lacks scientific basis for its intended purpose. The prior art method can easily result in the over application of acidic amendments, which results in plant toxicity. Over-acidification can cause calcium, magnesium, potassium, phosphorous and sulfur deficiencies. It can additionally cause toxicity of microelements such as manganese, iron, zinc, and aluminum as noted by Brady and Weil in 2008. Additionally, the prior art method fails to consider the effect of soil organic matter, despite the fact that it is known that soil organic matter constitutes an important source of hydroxyl and hydrogen ions.

Moreover, even if the prior art techniques based upon soil textural class were accurate, it is tedious and time consuming to determine in which textural class a particular soil fits. The most prevalent way of accurately determining soil classification is by sedimentation, using Stokes' Law to determine the relative amounts of sand, silt, and clay in a given soil. This method takes hours and is too time consuming to apply on a wide scale basis. Illustrating by example, the hydrometer method readings must be taken at 40 seconds and then after 7.72 hours to determine the percentages of silt and clay, respectively.

While there are other methods of determining soil texture, including the pipet method and the sieving method, such methods are neither cheap nor fast. Each involves laborious pretreatment and preparation of the soil. Each also involves specialized equipment like hydrometer, pipette, mixer and cylinder. Chemicals like hydrogen peroxide, sodium metaphosphate, or Calgon.sup.™ solution are needed. A trained lab technician is required.

In view of these deficiencies, many soil-testing laboratories simply use crude estimations of soil texture to make acidic amendment recommendations. For instance, while there are generally twelve soil textural classifications, many soil-testing laboratories limit the classifications considered for making acidic amendment recommendations to only three to make recommendation determinations simpler. Such processes make acidifying recommendations based upon anecdotal data depending upon whether a soil is sandy, loamy, or clayey. Some laboratories use a single acidifying recommendation based upon loam soils, multiplying it by one-third for sandy soils and increasing by one-half for clayey soils. Growers of acid loving crops rely upon such recommendations, despite the fact that the only basis for the same was that there are more colloidal sites on clay, less on loam, and far less on sand. If a recommendation was four pounds of an amendment per acre, and a grower inquires about what happens if five pounds per acre are added, the prior art method offered no guidance as to what the result would be.

Advantageously, embodiments of the present disclosure provide methods and systems with scientific basis that offer a recommendation for the correct application of soil acidifying materials, especially for poorly buffered soils. Advantageously embodiments of the disclosure work to avoid over acidifying. Embodiments of the disclosure provide a buffer solution that is capable of rapidly estimating the amount of acidifying materials is needed to lower soil pH to a target value. Advantageously, and unlike the acid buffer solutions for liming requirement recommendations developed by Adams Evans and Shoemaker, buffer solutions in accordance with the present disclosure do not use hazardous materials. Moreover, creating such buffer solutions is simple, quick, and inexpensive, with costs being demonstrated to be less than one cent per milliliter.

Embodiments of the disclosure provide fundamental laboratory protocols and mathematical relationships that make possible the use of a novel buffer solution for obtaining an acidic amendment requirement for soils. By detecting the change in pH of the buffer solution when applied to a soil solution, embodiments calculate the amount of acidic amendment needed by the soil to lower pH to the desired target value a function of the initial pH, the resultant pH, and the target pH by using the following relationships:

$$\text{Exchangeable Basicity (BC)} = (\text{Resultant pH} - \text{Buffer pH})/0.25 \quad (1)$$

$$\text{Elemental Sulfur to Add (S) (lb/A)} = BC^*(\text{Resultant pH} - \text{Buffer pH})^*(\text{Target pH} - \text{Initial pH})/(\text{Buffer pH} - \text{Target pH}) \quad (2)$$

where initial pH comprises the pH of a soil solution comprising a predetermined amount, e.g., 10 grams, of a selected soil sample wetted with a predetermined amount, e.g., 10 milliliters, of one or deionized or distilled water, the buffer pH is the pH of a buffer solution comprising compounds to displace alkaline anions from soil colloids of the soil solution with a displacement agent and to neutralize the alkaline anions with a neutralization agent in a buffer, the resultant pH is a pH of the soil solution when a predetermined amount, e.g., 10 milliliters, of the buffer solution is added, and the target pH is the desired pH of soil after an acidifying amendment is added. The exchangeable basicity can be calculated from measured pH values, as shown in equation (1) above. However, for simplicity, in some embodiments an average value can be used. It has been determined from experimentation on numerous samples that one suitable average value for the exchangeable basicity is 4. Where the buffer pH is established between 4.38 and 4.42, preferably 4.4, the equation (2) above can be expressed as follows:

$$\text{Elemental Sulfur to Add (S) (lb/A)} = 4^*(\text{Resultant pH} - 4.4)^*(\text{Target pH} - \text{Initial pH})/(4.4 - \text{Target pH}) \quad (3)$$

It has been determined from practicing the disclosed methods on a wide range of poorly buffered soil types that do not have free carbonate parent materials that accurate recommendations for acidifying amendments can be readily determined. It has been determined from practicing the methods and using the systems herein that accurate acidifying amendment recommendations can be obtained for soils that do not have a lot of exchangeable sites on their colloids and that do not have a continuous source of basicity such as hydroxide ions, carbonate ions, or bicarbonate ions. It has further been determined that the methods and systems described herein are also applicable for obtaining recommendations for acid requirements to reduce the pH in hydroponic systems.

In one or more embodiments, methods for obtaining the acid requirement determination of soil employs a buffer solution made up of the following components in a liter of solution: 0.75 milliliters concentrated (36 percent) acetic acid, 0.48 grams of ammonium acetate, 0.465 grams of ammonium fluoride and 1.5 grams of monobasic potassium phosphate. The solution is mixed together in approximately 0.5 liters of deionized or distilled water and is allowed to equilibrate for a predetermined amount of time, such as about ten minutes. In one or more embodiments, the target pH of the buffer solution is between 4.0 and 5.0, preferably between 4.38 and 4.42, and preferably about 4.4. In one or more embodiments, the buffer pH is intended to be 4.4 in a 1:1 ratio with water. Where it is not initially, the pH can be adjusted by adding one of a few drops of dilute acetic acid (to lower the pH) or potassium hydroxide (to raise the pH) if necessary.

The buffer solution can be added to a predetermined amount of a selected soil mixed with deionized or distilled water at a 1:1 ratio to form a solution. For example, ten grams of soil can be added to 10 milliliters of distilled or deionized water. The resultant mixture can be stirred to form a solution. In one embodiment, the solution can be allowed to equilibrate for a predetermined amount of time, such as thirty minutes. After this time, an initial pH can be measured using a standard ion-selective electrode.

In one embodiment, once this initial measurement is taken, a predetermined amount of the buffer solution can be added to the soil solution. In one embodiment, the predetermined amount is ten milliliters so that the resulting mixture is at a 1:1:1 ratio, with one part soil, one part water, and one part buffer solution. Again, the pH can be measured to obtain the resultant pH. Again, this measurement can be made with a standard ion-selective electrode.

The buffer solution displaces the high pH causing anions such as hydroxyl, bicarbonate and carbonate anions with fluoride and phosphate ions. Once they are displaced, the buffer neutralizes them with hydrogen that is generated from acetic acid. Ammonium acetate and monobasic potassium phosphate provide buffering capacity to the solution. When large amount of high pH causing anions are produced, more acid will be consumed to neutralize them and as the result, the pH of the acid buffer and soil solution will increase. Equations 1 and 2, or alternatively equation 3, then provides a recommendation of the amount of elemental sulfur required, expressed in pounds per acre, that is a function of the exchangeable basicity of the soil.

Using the buffer solution, it has been demonstrated that every 0.01 pH unit increase from initial buffer pH, i.e., 4.4, corresponds to approximately 0.004 meq of exchangeable basicity for a ten-gram sample of soil in ten milliliters of water. It should be noted that the methods and systems will offer no recommended acid amendment if either equation (2) or (3) above is negative.

Embodiments of the disclosure are novel over prior art methods. There is no similarity between embodiments of the disclosure and prior art methods. In contrast to prior art methods that depend upon soil textural classes, and further fail to include any contribution of soil organic matter, embodiments of the disclosure understand that soil acidity or basicity is a function of specific chemical reactions. Advantageously, embodiments of the disclosure obtain recommendations for acidifying amendment requirements as a function of chemical reactions. To wit, the buffer solution described herein, which is used for acid requirement determinations, reacts with high pH causing cations after displacing them from soil colloids. Advantageously, methods and systems described herein are based upon scientific principles derived from chemical reactions and measurements of buffering quantities of high pH causing anions.

Embodiments of the disclosure understand that soil pH is a very important soil property. It is sometimes referred to as the "master variable" in soil analysis. Embodiments of the disclosure contemplate that soil pH affects soil physical, chemical and biological properties. Clay and organic matter stability is affected by soil pH. Multiple chemical reactions that involve oxidation, reduction, precipitation and dissolution are significantly impacted by soil pH. Billions of soil microbes flourish at a specific soil pH. Plants grow at specific soil pH. Hence, quantifying and adjusting soil pH to appropriate values under specific condition is a vital agronomic and environmental task.

Turning now to FIG. 1, illustrated therein is a method 100 for preparing a buffer solution in accordance with one or more embodiments of the disclosure. At step 101, the method 100 includes providing a predetermined amount of one or more of deionized water or distilled water. For example, 0.5 liters of deionized or distilled water may be provided in a beaker, jar, or other container at step 101.

At step 102, a predetermined amount of acetic acid is added to the deionized or distilled water provided at step 101. For example, in one embodiment between 0.7 and 0.8 milliliters of acetic acid is added at step 102. In one embodiment, the acetic acid added at step 102 is a concentrated (e.g., with a concentration of between 30 and 40 percent) acetic acid. The addition of acetic acid to the deionized or distilled water at step 102 results in a solution.

At step 103, the method 100 includes adding a predetermined amount of ammonium acetate to the solution of step 102. In one embodiment, between 0.45 g/L and 0.50 g/L of ammonium acetate is added at step 103. At step 104, the method 100 includes adding a predetermined amount of monobasic potassium phosphate. In one embodiment, between 1.4 g/L and 1.6 g/L of the monobasic potassium phosphate is added at step 104. At step 105, the method 100 includes adding a predetermined amount of ammonium fluoride. In one embodiment, between 0.2 g/L and 0.3 g/L of ammonium fluoride is added at step 105.

At step 106, the resulting solution is mixed to dissolve the ammonium acetate, the monobasic potassium phosphate, and the ammonium fluoride added at steps 103, 104, 105, respectively. At step 107, the method 100 optionally includes waiting for a predetermined duration for the solution to equilibrate. At step 108, the method 100 includes measuring a pH of the resulting solution. In one embodiment, this measurement is made with a standard ion selective electrode pH meter that has been cleaned and calibrated.

The target pH should be between 4.0 and 5.0, preferably between 4.38 and 4.42, and preferably 4.40, as determined at decision 109. It has been determined by experimental testing that equations (1)-(3) above are more accurate when the buffer pH is 4.4. However, it has been determined that the equations work well when the pH of the buffer solution is between 4.38 and 4.42, which provides a laboratory tolerance range about the target of 4.40. Accordingly, in one embodiment decision 109 determines whether the pH of the buffer solution is between 4.38 and 4.42.

Where the pH is not within this range, it can be adjusted. For example, at step 110 when the pH is too low, it can be adjusted to between 4.38 and 4.42 by adding additional acetic acid. By contrast, when the pH is too high, at step 111 the buffer can be adjusted to between 4.38 and 4.42 by adding potassium hydroxide. In one or more embodiments, the acetic acid used at step 110, or alternatively the potassium hydroxide used at step 111, is 1 normal in concentration.

At step 112, the solution is normalized to a multiple of one liter by adding additional deionized or distilled water. At step 113, a selected sample of soil can be tested in accordance with the method of FIG. 3 using the buffer solution.

The following examples are provided to illustrate the practice of making the buffer solution by the method of FIG. 1. It should be noted that it is recommended that step 102 follow step 101. However, remaining steps can be performed in various orders. The examples are not intended to illustrate the complete range of compositions possible.

Example 1

A buffer solution was prepared using the method of FIG. 1 as follows: 500 milliliters of deionized water was placed in a container. Then 0.75 milliliters of 36 percent concentration acetic acid was added to the water. Then 0.48 grams of dry ammonium acetate was added to the mixture. Next, 0.465 grams of dry ammonium fluoride was added to the mixture. Then 1.5 grams of dry monobasic potassium phosphate was added to the mixture. The mixture was then briefly stirred to dissolve the other ingredients. Additional deionized water was added to increase the amount of solution to 900 milliliters. The solution was then allowed to equilibrate for a period of ten minutes. After this period, the pH was measured with a standard ion selective electrode pH meter. As the pH was between 4.38 and 4.42, water was added to increase the amount of solution to 1000 milliliters.

Example 2

A buffer solution was prepared using the method of FIG. 1 as follows: 500 milliliters of deionized water was placed in a container. Then 0.75 milliliters of 35 percent concentration acetic acid was added to the water. Then 0.48 grams of dry ammonium acetate was added to the mixture. Next, 0.465 grams of dry ammonium fluoride was added to the mixture. Then 1.5 grams of dry monobasic potassium phosphate was added to the mixture. The mixture was then briefly stirred to dissolve the other ingredients. Additional deionized water was added to increase the amount of solution to 900 milliliters. The solution was then allowed to equilibrate for a period of ten minutes. After this period, the pH was measured with a standard ion selective electrode pH meter. The pH measured above 4.42. Two drops of 1 normal acetic acid were added to the solution. The solution was allowed to equilibrate. The pH was remeasured, and found to be between 4.38 and 4.42, water was added to increase the amount of solution to 1000 milliliters.

Example 3

A buffer solution was prepared using the method of FIG. 1 as follows: 500 milliliters of deionized water was placed in a container. Then 0.75 milliliters of 37 percent concentration acetic acid was added to the water. Then 0.48 grams of dry ammonium acetate was added to the mixture. Next, 0.465 grams of dry ammonium fluoride was added to the mixture. Then 1.5 grams of dry monobasic potassium phosphate was added to the mixture. The mixture was then briefly stirred to dissolve the other ingredients. Additional deionized water was added to increase the amount of solution to 900 milliliters. The solution was then allowed to equilibrate for a period of ten minutes. After this period, the pH was measured with a standard ion selective electrode pH meter. The pH measured below 4.38. One drop of 1 normal potassium hydroxide was added to the solution. The solution was allowed to equilibrate. The pH was remeasured, and found to be between 4.38 and 4.42, water was added to increase the amount of solution to 1000 milliliters.

Figure 2:
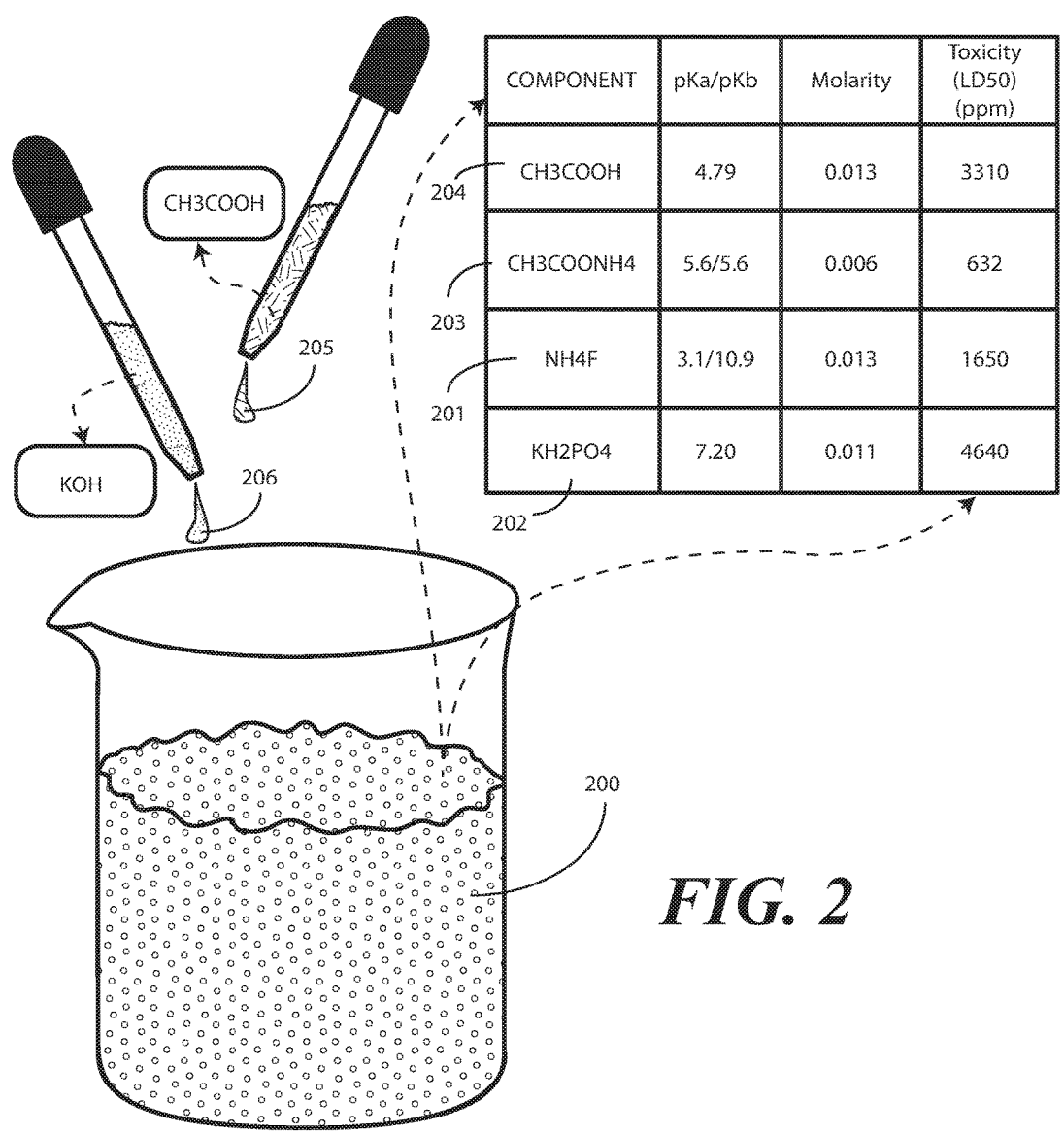
FIG. 2 illustrates one explanatory buffer solution in accordance with one or more embodiments of the disclosure.

Turning now to FIG. 2, illustrated therein is the buffer solution 200 produced using the method of FIG. 1. As shown in the figure, in one embodiment the buffer solution 200 includes a soil colloid alkaline anion displacement agent 201 comprising one or more of ammonium fluoride or monopotassium phosphate. In this illustrative embodiment, the soil colloid alkaline anion displacement agent 201 comprises acetic acid present in the solution with a molarity of 0.013. In one or more embodiments, the acetic acid is present at a concentration of between 0.2 g/L and 0.3 g/L in the buffer solution 200.

The buffer solution 200 of FIG. 2 also includes a buffer. In this embodiment, the buffer comprises a combination of monobasic potassium phosphate 202 and ammonium acetate 203. The monobasic potassium phosphate 202 is present at a concentration of 0.011 moles per liter, while the ammonium acetate 203 is present at a concentration of 0.0006 moles per liter.

The buffer solution 200 also includes a soil colloid alkaline anion neutralization agent 204. In this illustrative embodiment, the soil colloid alkaline anion neutralization agent 204 comprises acetic acid, which is present at a concentration of 0.013 moles per liter.

Accordingly, in one or more embodiments the buffer solution 200 consists essentially of 0.013M acetic acid ($CH_3COOH$), 0.006M ammonium acetate ($CH_3COONH_4$), 0.013M ammonium fluoride ($NH_4F$), and 0.011M monobasic potassium phosphate ($KH_2PO_4$ (0.011M). This buffer solution 200 reacts with alkaline soils and displaces the causing anions through exchange reactions of fluoride ions ($F^-$) and dihydrogen phosphate ($H_2PO_4^-$). These anions are then neutralized by the acetic acid. The buffer solution 200 buffers around the listed kPa and kPb of the constituent components.

The buffer solution 200 contains chemicals that displace alkaline anions and neutralizes them. Complete displacement and neutralization was achieved within an hour even though the buffer pH of ten or fewer samples continued to increase by 0.20 buffer pH units over a three-day observation period. The buffer solution 200 should be mixed well as soon as the buffer components, i.e., the combination of monobasic potassium phosphate 202 and ammonium acetate 203, are added. Buffer pH measurements can be taken while stirring the buffer solution 200. The pH of the buffer solution 200 of FIG. 2 is 4.40. However, it can be adjusted using 1 normal acetic acid 205 or 1 normal potassium hydroxide 206 if necessary.

Illustrating by example, if acetic acid with a 36 percent concentration was desired, but the acetic acid percentage was instead 35 percent or 37 percent due to measurement inaccuracies, the measured pH of the buffer solution 200 will be slightly different from the desired 4.4. Consequently adjustment may be required. Accordingly, in one or more embodiments, the buffer solution 200 can also include a few drops of potassium hydroxide 206 to increase the pH, or a few drops of acetic acid 205 to reduce the pH. Where adjustment is required, the amount of 1 normal acetic acid 205 or 1 normal potassium hydroxide 206 should be just a few drops, and will not be more than one milliliter or so.

The buffer solution 200 of FIG. 2 constitutes a dilute buffer. Additionally, it has been determined that all constituent components mix or dissolve easily under normal laboratory conditions. No special handling of the components is required other than standard laboratory protocols that will be obvious to those of ordinary skill in the art having the benefit of this disclosure.

Figure 3:
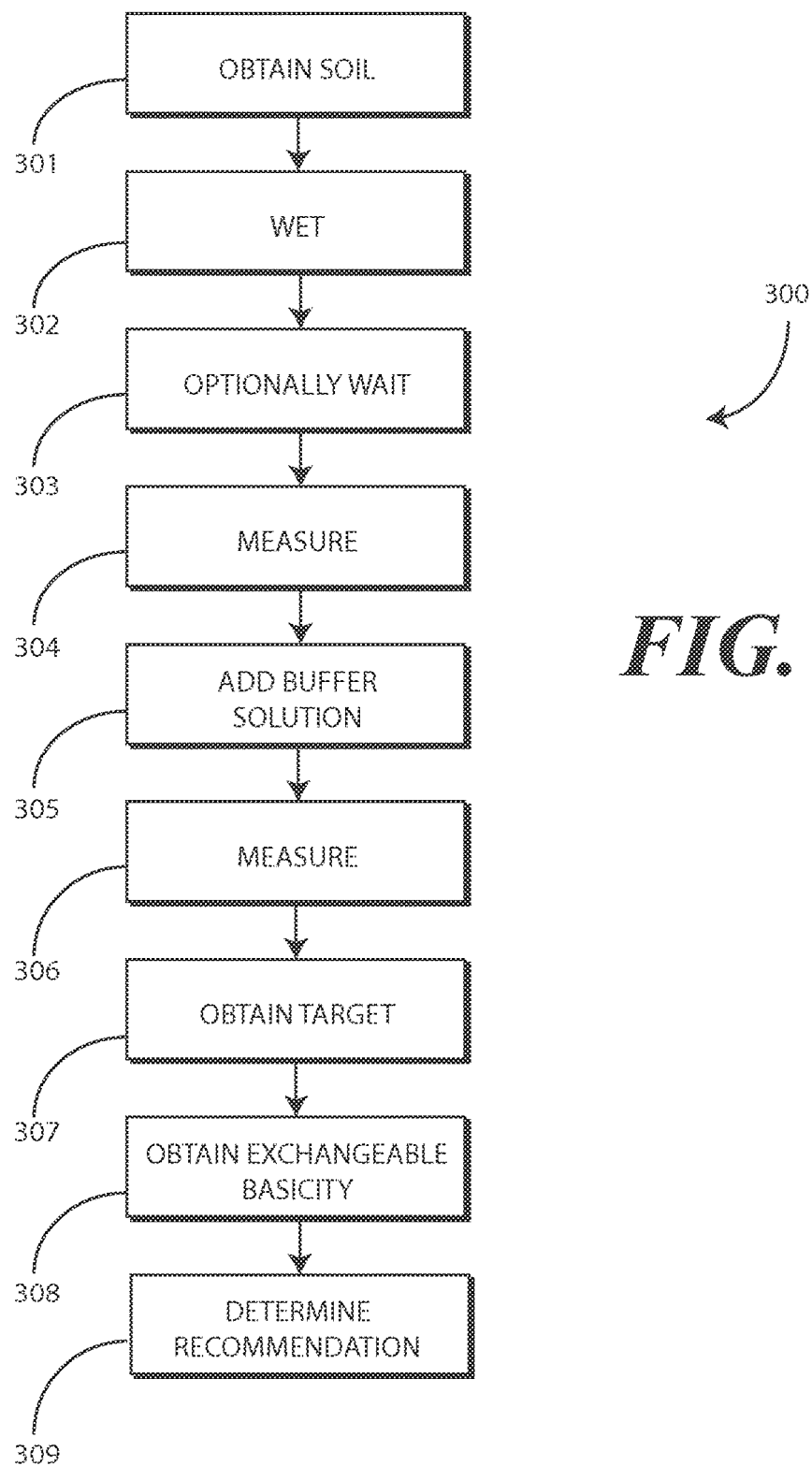
FIG. 3 illustrates another explanatory method in accordance with one or more embodiments of the disclosure.

Turning now to FIG. 3, illustrated therein is one explanatory method 300 of testing soil in accordance with one or more embodiments of the disclosure. At step 301, a selected sample of soil is provided. In one embodiment, the selected sample obtained at step 301 is an oven-dried sample with a predetermined mass, such as ten grams.

At step 302, the method 300 includes wetting the selected soil sample with one or more of deionized water or distilled water to obtain a soil solution. Step 302 can include stirring the selected soil sample in the deionized and/or distilled water. In one embodiment, the deionized and/or distilled water added at step 302 has a predefined volume. In one embodiment, the water is mixed with the soil at a 1:1 ratio. Thus, if ten grams of soil are used, ten milliliters of deionized or distilled water will be added at step 302.

At step 303, the method 300 optionally includes waiting a predetermined duration after the wetting occurring at step 302. For example, it has been determined in laboratory tests that waiting a duration of thirty minutes after wetting the soil sample allows for maximum displacement of anions by the buffer solution.

At step 304, the method includes measuring an initial pH of the soil solution. In one embodiment, this step 304 includes measuring the initial pH of the soil solution with a standard ion selective electrode pH meter while the solution is being stirred.

At step 305, a buffer solution is added. In one embodiment, the buffer solution is added at a 1:1:1 ratio to the water of step 302 and the soil of step 301. Accordingly, if ten grams of soil are selected at step 301, and ten milliliters of deionized or distilled water are added at step 302, ten milliliters of the buffer solution will be added at step 305.

In one embodiment, the buffer solution is chemically operable to displace alkaline anions from soil colloids of the soil solution with a displacement agent. The buffer solution is also chemically operable to neutralize the alkaline anions with a neutralization agent in a buffer having a buffer pH of between 4.38 and 4.42. For example, the displacement agent can comprise ammonium fluoride, while the neutralizing agent comprises acetic acid and the buffer comprises a mixture of monobasic potassium phosphate and ammonium acetate as previously described.

Step 305 can optionally include preparing the buffer solution. In one embodiment, step 305 includes preparing the buffer solution by mixing one or more of ammonium fluoride or monopotassium phosphate with the following: ammonium acetate; acetic acid; and water. Step 305 can optionally include adjusting the buffer pH to between 4.38 and 4.42 by one of adding additional amounts of the acetic acid to the buffer solution to reduce the buffer pH or adding potassium hydroxide to the buffer solution to increase the buffer pH.

At step 306, the method 300 includes measuring a resultant pH of the soil solution after applying the buffer solution at step 305. At step 307, a target pH of the selected soil sample after application of an acidifying amendment is selected.

At step 308, the exchangeable basicity of the soil sample is obtained. In one embodiment, the exchangeable basicity of the soil sample is calculated from the initial pH and the resultant pH using equation 1 above. As noted above, where all samples are sufficiently similar, an average value can be selected instead. For example, it has been determined that an average value of four is appropriate for soils from the state of Alabama by testing over forty different samples. Other regions and areas may have different average values that are obvious to those of ordinary skill in the art having the benefit of this disclosure.

At step 309, an acidic amendment requirement as a function of the initial pH, the resultant pH, and the target pH is obtained. In one embodiment, the acidic amendment requirement is calculated directly using equation (2) above as a function of the measured exchangeable basicity. In another embodiment, where an average exchangeable basicity is used, the acidic amendment requirement is calculated directly using equation (3) above. The formula for the acidic amendment requirement thus can take the general form:

$$\text{Acidic Amendment Requirement (lb/A)} = (X^*(\text{buffer pH}-\text{resultant pH})^*(\text{target pH}-\text{initial pH}))/(\text{buffer pH}-\text{target pH}) \quad (4)$$

where X comprises an exchangeable basicity factor, be it calculated or a selected average. In one or more embodiments, this results in the acidic amendment requirement being expressed in units of weight of elemental sulfur per unit area. However, embodiments of the disclosure contemplate that one may select a different amendment, e.g., sulfuric acid, aluminum sulfate, ferrous sulfate, reduced nitrogen, sulfur containing fertilizers, and organic material. Conversion factors used to translate measurements of elemental sulfur to these various materials are known in the art and will be obvious to those of ordinary skill in the art having the benefit of this disclosure.

The following example is provided to illustrate the practice of testing a selected soil sample by the method of FIG. 3. The examples are not intended to illustrate the complete range of compositions possible.

Example 4

Forty ten-gram soil samples of soil were randomly selected from samples submitted to the Auburn University Soil Testing Laboratory in accordance with the following criteria: The soils should have a pH of 6.5 or higher and no known carbonate parent material. However, soils that have different exchangeable cations were included. Each sample was wetted at a 1:1 ratio with ten milliliters of deionized water. The samples were mixed and were allowed to equilibrate for thirty minutes. The initial pH of the soil solution of each sample was measured while stirring the solution. The initial pH varied widely across the forty samples. The average physic-chemical properties were determined following standard lab procedures set forth by Hue and Evans (1986).

Next, ten milliliters of the buffer solution (200) of FIG. 2 were added so that the resulting solution was in a 1:1:1 ratio. The resultant pH was measured to the nearest 0.01 pH unit after an hour, again while stirring. The pH of the buffer with 1:1 deionized water, control solution, was 4.40. The base saturation, and acid requirement were calculated using equations (1) and (2), respectively, as given above.

Figure 4:
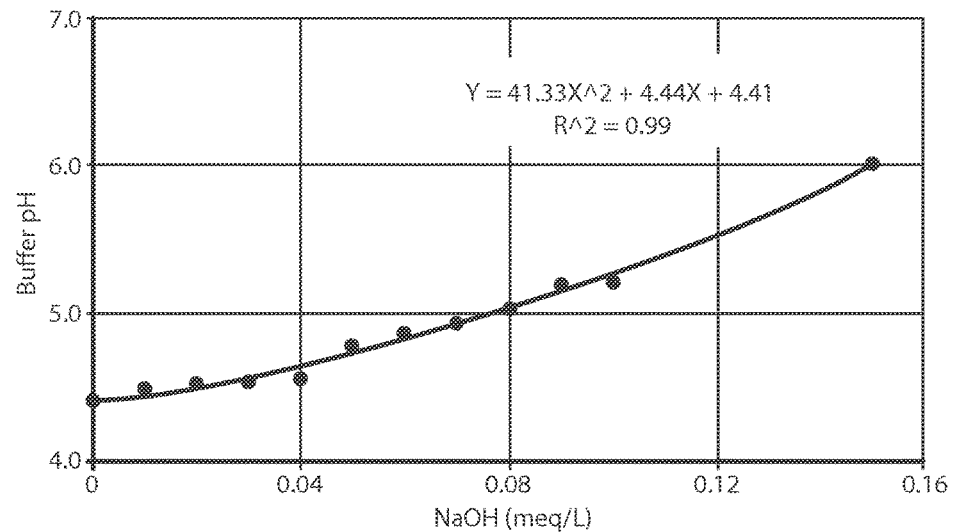
FIG. 4 illustrates an explanatory graph demonstrating a relationship between buffer pH and sodium hydroxide in accordance with one or more embodiments of the disclosure.
Figure 5:
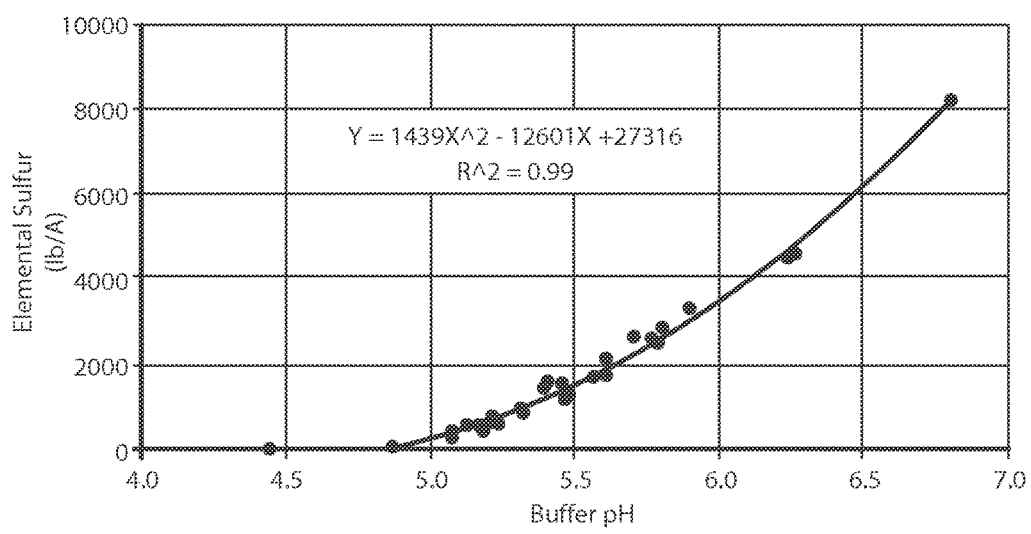
FIG. 5 illustrates an explanatory graph demonstrating a relationship between an amount of elemental sulfur per unit area required to change a pH of a selected soil to a target pH as a function of buffer pH when the selected soil is subjected to the buffer in accordance with one or more embodiments of the disclosure.

General linear model SAS programs (SAS System, 1990) were then used to generate quadratic equations and correlation values for the buffer solution and NaOH reaction (FIG. 4) and the amount of elemental sulfur needed (FIG. 5).

The average values of selected properties of the soils are shown below in Table 1.

TABLE 1

| Number Samples | Initial pH | Resultant pH | Exchangeable H (cmolc/kg) | CEC (buffer) (cmolc/kg) |
|---|---|---|---|---|
| 40 | 6.94 | 5.3 | 1.62 | 9.81 |

The average percent acid saturation of the soil samples was 16.5 percent, while the percent base saturations was 83.5 percent. This was expected for soils that have an average water pH of 6.94 in the region. The soils are poorly buffered as indicated by the relatively low effective cation exchange capacity.

The elemental sulfur needed to adjust high pH soils to pH 5.0 and 6.0 are given in Table 2.

TABLE 2

| Initial pH | RESULTANT pH | | | | | | | |
|---|---|---|---|---|---|---|---|---|
| | 4.5 | 4.6 | 4.8 | 5.0 | 5.2 | 5.4 | 5.6 | 5.8 | 6.0 |
| Hundreds of elemental S | | | | | | | | |
| Target pH = 5.0 | | | | | | | | |
| 9.0 | 4 | 9 | 17 | 26 | 34 | 43 | 51 | 60 | 68 |
| 8.5 | 4 | 7 | 15 | 22 | 30 | 37 | 45 | 52 | 60 |
| 8.0 | 3 | 6 | 13 | 19 | 26 | 32 | 38 | 45 | 51 |
| 7.5 | 3 | 5 | 11 | 16 | 21 | 27 | 32 | 37 | 43 |
| 7.0 | 2 | 4 | 9 | 13 | 17 | 21 | 26 | 30 | 34 |
| 6.5 | 2 | 3 | 6 | 10 | 13 | 16 | 19 | 22 | 26 |
| 6.0 | 1 | 2 | 4 | 6 | 9 | 11 | 13 | 15 | 17 |
| 5.5 | 1 | 1 | 2 | 3 | 4 | 5 | 6 | 7 | 9 |
| 5.0 | 0 | 0 | 0 | 0 | 0 | 0 | 0 | 0 | 0 |
| Target pH = 6.0 | | | | | | | | |
| | 4.5 | 4.6 | 4.8 | 5.0 | 5.2 | 5.4 | 5.6 | 5.8 | 6.0 |
| 9.0 | 1 | 2 | 5 | 7 | 10 | 12 | 14 | 17 | 19 |
| 8.5 | 1 | 2 | 4 | 6 | 8 | 10 | 12 | 14 | 16 |
| 8.0 | 1 | 2 | 3 | 5 | 6 | 8 | 10 | 11 | 13 |
| 7.5 | 1 | 1 | 2 | 4 | 5 | 6 | 7 | 8 | 10 |
| 7.0 | 0 | 1 | 2 | 2 | 3 | 4 | 5 | 6 | 6 |
| 6.5 | 0 | 0 | 1 | 1 | 2 | 2 | 2 | 3 | 3 |
| 6.0 | 0 | 0 | 0 | 0 | 0 | 0 | 0 | 0 | 0 |

It was determined that the initial pH of the soil solution is an indicator whether acidifying of a given soil is necessary. In general, it was determined that the amount of elemental sulfur required to lower a soil pH is dependent on the base buffering capacity of a soil and the target pH, which is selected by the need of a target crop. As the difference between the initial pH of the soil solution and the buffer pH increases, the amount of elemental sulfur recommended to reach a target value increases. The reverse is true for smaller differences between buffer pH and the resultant pH of the soil solution combined with the buffer.

As shown in FIG. 4, buffer solutions in accordance with embodiments of the present disclosure resist abrupt changes in pH, as illustrated the titration of the buffer solution with NaOH. The relationship was determined to be quadratic and offered a high correlation as indicated by a r-squared value near one. Buffer solutions in accordance with embodiments of the disclosure are expected to measure the capacity (fraction of reserve, exchangeable and soluble basicity) and the intensity (soil solution basicity) factors of soil acidity.

As shown in FIG. 5, the relationship between elemental sulfur recommended to decrease soil pH to a target value of 5.0 versus the buffer pH is shown. Again, for this forty-sample test, the quadratic correlation was high, with the r-squared value again at almost one. Only a few samples required more than two tons of elemental S to change the soil solution pH to 5.0. This is expected since these soils are poorly buffered in terms soil basicity. The few differences observed may be attributable to an abundance of organic matter with hydroxyl ions. Alternatively, they may represent recently limed samples and/or high content of silicate clays.

To confirm performance of the methods and systems described herein, an alternate analysis was performed on the results. In 1962, Adams and Evans (1962) developed a quadratic relationship between soil solution pH and degree of acid saturation (Hsat1) by applying the least square statistical method to determine the best-fit equation. A solution of the quadratic equation for soil water pH and desired pH (Hsat2) were used to determine the amount of liming material needed. The equations are given as follows:

$$\text{Measured soil pH} = 7.79 - 5.55 * H\text{sat1} + 2.227 * (H\text{sat1})^2, \quad (5)$$

$$CaCO_3 \text{ (Mg/ha)} = (8000(8 - \text{buffer pH})) * (H\text{sat1} - H\text{sat2}) * (1.5) \times 2.24, \quad (6)$$

where Hsat1 and Hsat2 represent the base unsaturation of soil at measured and desired pH, respectively. The solution of equation (5) was incorporated into equation (6) to determine the amount of lime required to raise pH of a given soil to a targeted pH at base unsaturation, Hsat2.

Figure 6:
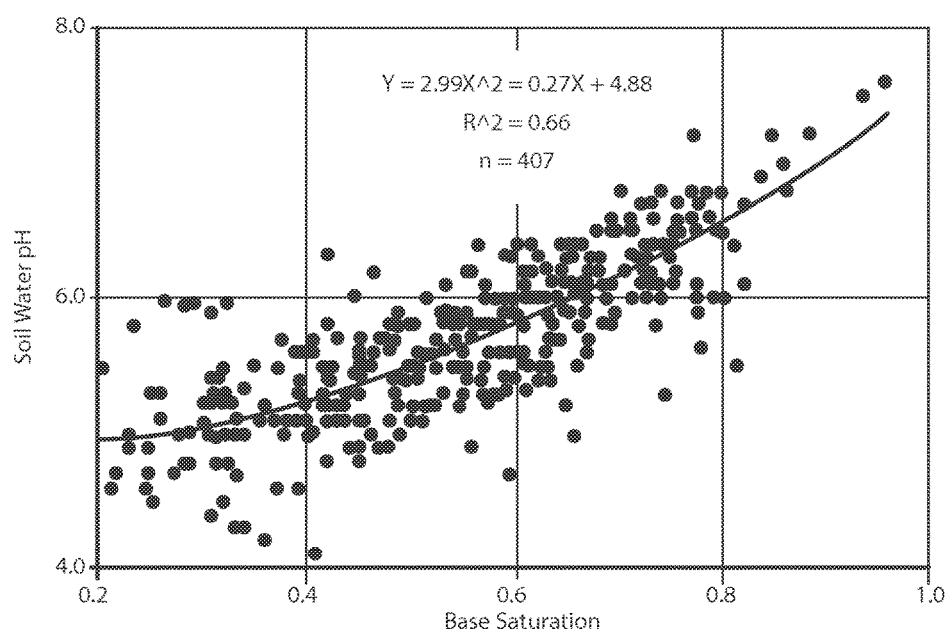
FIG. 6 illustrates an explanatory graph demonstrating correlation between a soil solution pH and base saturation of a selected soil in accordance with one or more embodiments of the disclosure.

It has been determined that the relationship between pH and base unsaturation may not be the same for all soils. This introduces inherent uncertainty in the method. The present inventor has demonstrated that it is possible to develop a different equation (5) above for different soils that may result in different base saturation calculations and acid recommendations since base saturation is equal to one minus the acid saturation (Huluka, 2005). The quadratic relationship between soil water pH and base saturation was highly significant as shown in FIG. 6. Thus, equations (5) and (6) above can be modified as follows:

$$\text{Measured soil pH} = 4.88 - 0.27 * B\text{sat1} + 2.99 * (B\text{sat1})^2 \quad (7)$$

$$CaCO_3 \text{ (Mg/ha)} = (8000(8 - \text{buffer pH})) * (B\text{sat1} - B\text{sat2}) * (1.5) * 2.24, \quad (8)$$

where Bsat1 and Bsat2 represent the base saturation of soil at measured and desired pH, respectively. It was determined that the higher the water pH of the soil, the lower the base unsaturation and vise versa. The quadratic equation for the relationship was very similar to the Adams-Evans original equation given above, but necessary adjustment had to be made for the equation to be used as acid requirement solution. Depending on the relationship between soil water pH and base saturation, different quadratic equations can be formulated for different soils that will also affect acid recommendations.

Accordingly, in this example a test of forty soil samples used to verify the methods and systems described above to provide recommended amounts of amount of elemental sulfur needed to change the pH of a selected soil to a target that was lower that the pH measured when the soil was in solution. The methods and systems described above are unique in that no other systems or methods previously set forth uniquely present a buffer solution composition operable to determine the amount of acidifying materials needed to reduce a soil pH. The simple methods and systems described above will be beneficial to the many blueberry and azalea farmers who may no more have to depend on soil textural class analysis to acidify their soils. Experimental testing has confirmed that the buffer solution and corresponding methods and systems work effectively in laboratory environments. Moreover, buffer solutions in accordance with embodiments of the disclosure are environmental friendly and non-toxic, in contrast to the Adams Evans and Shoemaker buffer solutions mentioned above.

It should be emphasized that the above-described embodiments of the buffer solutions, systems, and methods are merely possible examples of implementations of the buffer solutions, systems, and methods, and are merely set forth for a clear understanding of the principles set forth herein. Many variations and modifications may be made to the buffer solutions, systems, and methods disclosed herein without departing substantially from the spirit and principles of the disclosure. All such modifications and variations are intended to be included herein within the scope of this disclosure and the following claims.

Illustrating by example, those of ordinary skill in the art having the benefit of this disclosure will readily recognize that for universal applicability, more samples than the forty-sample set may have to be used, and that the equations set forth herein may change as a function of that analysis for an average group of soils. The equations herein work for poorly buffered soils, i.e., those that have a low cation exchange capacity. Also, the methods, buffer solutions, and examples above are soils that do not have a permanent source of basicity. However, the methods, buffer solutions, and systems described herein work well in practice (as demonstrated by testing over 400 soil samples) and are presently being used at the Auburn University Soil Testing Laboratory to make acidic amendment requirement recommendations.

Figure 7:
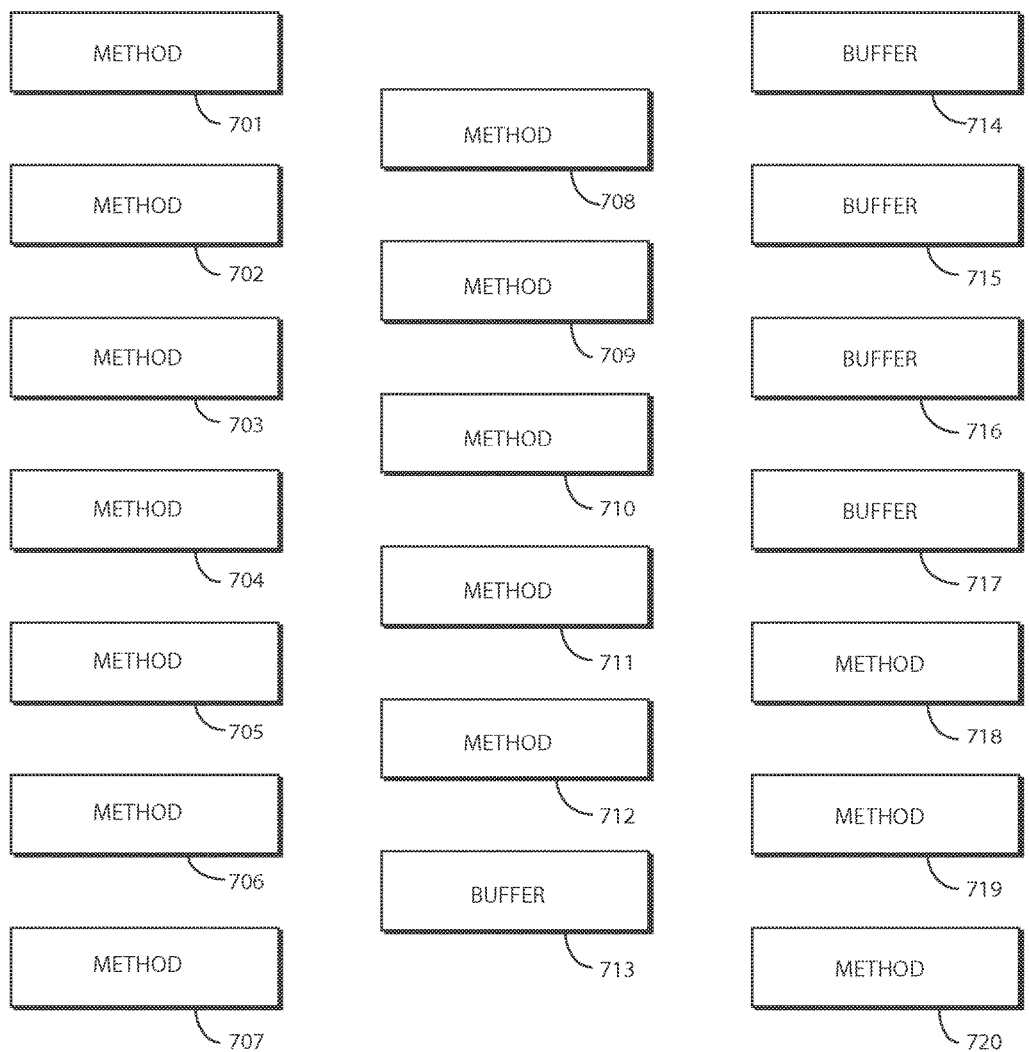
FIG. 7 illustrates various embodiments of the disclosure.

Turning now to FIG. 7, illustrated therein are various embodiments of the disclosure. At 701, a method of testing soil comprises wetting a selected soil sample with one of deionized water or distilled water to obtain a soil solution. At 701, the method includes measuring an initial pH of the soil solution and applying a buffer solution to the soil solution. In one embodiment, the buffer solution is chemically operable to displace alkaline anions from soil colloids of the soil solution with a displacement agent and neutralize the alkaline anions with a neutralization agent in a buffer having a buffer pH of between 4.38 and 4.42. In one embodiment, at 701 the method includes measuring a resultant pH of the soil solution after the applying the buffer solution, selecting a target pH for the selected soil sample, and obtaining an acidic amendment requirement as a function of the initial pH, the resultant pH, and the target pH.

At 702, the method of 701 further comprises determining an exchangeable basicity of the selected soil sample from the initial pH and the resultant pH. At 702 the function for the obtaining the acidic amendment requirement of 701 is further a function of the exchangeable basicity.

At 703, the method of 701 further comprises selecting the acidic amendment from the group consisting of elemental sulfur, sulfuric acid, aluminum sulfate, ferrous sulfate, reduced nitrogen, sulfur containing fertilizers, and organic material. At 704, the function for obtaining the acidic amendment requirement of 701 equals (X*(buffer pH−resultant pH)*(target pH−initial pH))/(buffer pH−target pH), wherein X comprises an exchangeable basicity factor.

At 705, the displacement agent of 704 comprises ammonium fluoride, while the neutralizing agent comprises acetic acid. At 705, the buffer of 704 comprises a mixture of monobasic potassium phosphate and ammonium acetate.

At 706, the acidic amendment requirement of 705 is expressed in units of weight of elemental sulfur per unit of area. At 707, the exchangeable basicity factor of 705 is selected to be an average value of 4 for simplicity. In another embodiment, the exchangeable basicity factor of 705 is selected to be an average value of 6.44 for simplicity.

At 708, the selected soil sample of 701 comprises about ten grams of soil by weight. At 708, the one of deionized water or distilled water of 701 comprises about ten milliliters of the one of deionized water or distilled water by volume, and the buffer solution of 701 comprises about ten milliliters of the buffer solution by volume.

At 709, the method of 701 further comprises waiting a predetermined duration between the wetting the selected soil sample and the measuring the initial pH. In one embodiment, this duration is about thirty minutes. At 710, the method of 701 further comprises preparing the buffer solution by mixing one or more of ammonium fluoride or monopotassium phosphate with the following: ammonium acetate; acetic acid; and water.

At 711, the method of 710 also includes adjusting the buffer pH to between 4.38 and 4.42. In one embodiment, 711 includes adding additional amounts of the acetic acid to the buffer solution to reduce the buffer pH. In another embodiment, 711 includes adding potassium hydroxide to the buffer solution to increase the buffer pH.

At 712, a buffer solution for testing soil includes the following: a soil colloid alkaline anion displacement agent comprising one or more of ammonium fluoride or monopotassium phosphate; a buffer comprising a combination of monobasic potassium phosphate and ammonium acetate; and a soil colloid alkaline anion neutralization agent comprising acetic acid. The buffer at 712 buffers the buffer solution at a pH between 4.0 and 5.0, preferably between 4.38 and 4.42 in accordance with the pKa/pKb quotient of the constituent components.

At 713, the soil colloid alkaline anion displacement agent of 712 comprises ammonium fluoride. At 713, the buffer solution of 712 comprises a dilute solution containing between between 0.45 g/L and 0.50 g/L of the aluminum fluoride.

At 714, the buffer solution of 713 comprises between 0.45 g/L and 0.50 g/L of the ammonium acetate and between 1.4 g/L and 1.6 g/L of the monobasic potassium phosphate. At 715, the soil colloid alkaline anion neutralization agent of 714 comprises between 0.2 g/L and 0.3 g/L of the acetic acid. At 716, the buffer solution of 715 contains less than one milliliter of potassium hydroxide to adjust the pH between 4.38 and 4.42 at 717.

At 718, a method of testing soil includes providing a predetermined amount of one of deionized water or distilled water, adding between 0.7 and 0.8 milliliters of acetic acid with a concentration of between 30 and 40 percent to the one of deionized water or distilled water to form a solution, and adding to the solution the following: between 0.45 g/L and 0.50 g/L of ammonium acetate; between 1.4 g/L and 1.6 g/L of the monobasic potassium phosphate; and between 0.2 g/L and 0.3 g/L of ammonium fluoride. At 718, the method includes mixing the solution to dissolve the ammonium acetate, the monobasic potassium phosphate, and the ammonium fluoride. At 718, the method includes waiting a predetermined duration and measuring a buffer pH of the solution.

At 719, the method of 718 includes optionally adjusting the buffer pH to between 4.38 and 4.42 by one of adding additional acetic acid to lower the buffer pH or adding potassium hydroxide to raise the buffer pH. At 720, the method of 718 includes adding a second predetermined amount of the one of deionized water or distilled water to the solution, obtaining a selected sample of soil, and combining the solution, water, and the selected sample of soil in a 1:1:1 ratio to obtaining an acidic amendment requirement for the selected sample of soil.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims. Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. A method of testing soil, comprising:
   providing a predetermined amount of one of deionized water or distilled water;
   adding between 0.7 and 0.8 milliliters of acetic acid with a concentration of between 30 and 40 percent to the one of deionized water or distilled water to form a first solution;
   adding to the first solution:
      between 0.45 g/L and 0.50 g/L of ammonium acetate,
      between 1.4 g/L and 1.6 g/L of monobasic potassium phosphate, and
      between 0.2 g/L and 0.3 g/L of ammonium fluoride to form a second solution;
   mixing the second solution to dissolve the ammonium acetate, the monobasic potassium phosphate, and the ammonium fluoride;
   waiting a predetermined duration; and
   measuring a buffer pH of the second solution.

2. The method of claim 1, further comprising adjusting the buffer pH to between 4.38 and 4.42 by one of adding additional acetic acid to lower the buffer pH or adding potassium hydroxide to raise the buffer pH.

3. The method of claim 1, further comprising:
   adding a second predetermined amount of the one of deionized water or distilled water to the second solution to form a third solution;
   obtaining a selected sample of soil;
   combining the third solution, the second predetermined amount of the one of deionized water or distilled water, and the selected sample of soil in a 1:1:1 ratio; to form a fourth solution; and
   obtaining an acidic amendment requirement for the selected sample of soil.

4. The method of claim 3, further comprising measuring a resultant pH of the fourth solution, after the third solution is combined with the second predetermined amount of the one of deionized water or distilled water and the selected sample of soil.

5. The method of claim 4, further comprising determining an exchangeable basicity for the selected soil sample from the buffer pH and the resultant pH.

6. The method of claim 5, wherein the acidic amendment requirement for the selected sample of soil is a function of the exchangeable basicity for the selected soil sample.

7. The method of claim 4, further comprising selecting an acidic amendment from the group consisting of elemental sulfur, sulfuric acid, aluminum sulfate, ferrous sulfate, reduced nitrogen, sulfur containing fertilizers, and organic material.

8. The method of claim 4, further comprising selecting a target pH for the selected sample of soil.

9. The method of claim 8, wherein the acidic amendment requirement for the selected sample of soil is a function of the buffer pH, the resultant pH, and the target pH.

10. The method of claim 9, wherein a formula for the function is the acidic amendment requirement equals (X*(buffer pH−resultant pH)*(target pH−initial pH))/(buffer pH−target pH), wherein X comprises an exchangeable basicity factor, and wherein initial pH is a pH of a soil solution comprising a predetermined amount of the selected sample of soil wetted with third predetermined amount of the one of deionized water or distilled water.

11. The method of claim 10, wherein the exchangeable basicity factor is 4.

12. The method of claim 3, wherein the acidic amendment requirement is expressed in units of weight of elemental sulfur per unit of area.

13. The method of claim 3, the selected sample of soil comprising at least ten grams of soil, the second predetermined amount of the one of deionized water or distilled water comprising at least ten milliliters of the one of deionized water or distilled water, and the fourth solution comprising at least ten milliliters of the third solution.

14. The method of claim 3, further comprising waiting a predetermined duration between combining the third solution, the second predetermined amount of the one of deionized water or distilled water, and the selected sample of soil in the 1:1:1 ratio and the obtaining an acidic amendment requirement for the selected sample of soil.

15. The method of claim 3, further comprising adding potassium hydroxide to the second solution.

* * * * *